(12) United States Patent
Cho et al.

(10) Patent No.: US 7,723,102 B2
(45) Date of Patent: May 25, 2010

(54) ENHANCED TRANSFECTION SYSTEM

(75) Inventors: Myung-Sam Cho, Pinole, CA (US); Helena Yee, San Francisco, CA (US)

(73) Assignee: Bayer Corporation, Pittsburgh, PA (US)

(*) Notice: Subject to any disclaimer, the term of this patent is extended or adjusted under 35 U.S.C. 154(b) by 0 days.

(21) Appl. No.: 09/956,576

(22) Filed: Sep. 18, 2001

(65) Prior Publication Data
US 2003/0059942 A1    Mar. 27, 2003

Related U.S. Application Data

(60) Provisional application No. 60/386,223, filed on Sep. 28, 2000.

(51) Int. Cl.
C12N 15/00    (2006.01)
C12N 15/11    (2006.01)
C12N 15/63    (2006.01)
C12N 15/67    (2006.01)
C12N 15/85    (2006.01)

(52) U.S. Cl. .............. 435/320.1; 435/69.1; 435/325; 536/23.1; 536/24.1

(58) Field of Classification Search ............ 435/6, 435/69.1, 320.1, 325, 440, 402, 326, 335, 435/346, 372.2, 369, 456; 536/23.5, 24.1, 536/24.2
See application file for complete search history.

(56) References Cited

U.S. PATENT DOCUMENTS

| | | | |
|---|---|---|---|
| 4,686,186 A | | 8/1987 | Sugden |
| 5,693,508 A | * | 12/1997 | Chang ........................... 435/6 |
| 5,716,845 A | * | 2/1998 | Sugden et al. ........... 435/372.2 |
| 5,801,056 A | | 9/1998 | Haseltine et al. |
| 5,854,021 A | | 12/1998 | Cho et al. |
| 5,976,807 A | * | 11/1999 | Horlick et al. .................. 435/6 |
| 6,136,599 A | * | 10/2000 | Cho .......................... 435/325 |
| 6,150,515 A | * | 11/2000 | Sharp et al. ................ 536/23.5 |
| 6,156,497 A | * | 12/2000 | Kaleko ........................... 435/5 |
| 6,218,187 B1 | * | 4/2001 | Finer et al. .................. 435/457 |
| 6,465,251 B1 | * | 10/2002 | Schultze et al. ............. 435/377 |

FOREIGN PATENT DOCUMENTS

| | | | |
|---|---|---|---|
| EP | 0292879 A2 | * | 11/1988 |
| EP | 0629700 A2 | | 12/1994 |
| WO | WO-99/60128 | * | 11/1999 |
| WO | WO-00/28060 A2 | | 5/2000 |
| WO | WO-01/98506 A2 | | 12/2001 |

OTHER PUBLICATIONS

F. Langle-Rouault et al. Up to 100-fold increase of apparent gene expression in the presence of Epstein-Barr virus oriP sequences and EBNA1: implications of the nuclear import of plasmids. J. Virol. (1998). 72(7): 6181-6185.*

Gahn et al. An EBNA1-Dependent Enhancer Acts from a Distance of 10 kilobase Pairs to Increase Expression of the Epstein-Barr Virus LMP Gene. J. of Virol. (1995) 69(4) 2633-2636.*

Markovitz et al. Disparate Effects of Two Herpesvirus Immediate-Early Gene trans-Activators on teh HIV-1- LTR. J. Virol. (1989). 173:750-754.*

Yates et al., Proc. Natl. Acad. Sci. USA 81:3806-3810 June 1984.

Lieberman et al., Journal of Virology 60:140-148 Oct. 1986 Baltimore MD.

Kenny et al., Journal of Virology 63:3870-3877 Sep. 1989 Baltimore MD.

Rovolo et al., Proc. Natl. Acad. Sci. USA 95: 8852-8857 Jul. 1998.

Tsang, T, C., et al., "Construction of New Amplifier Expression Vectors for High Levels of IL-2 Gene Expression", International Journal of Molecular Medicine, 2000, vol. 5, pp, 295-300.

Shen, E. S., et al., "improved Expression Cloning Using Reporter Genes and Epstein-Barr Virus *ori*-Containing Vectors", Gene, 1995, vol. 156, pp. 235-239.

Cachianes, G., et al., "Epstein-Barr Virus-Derived Vectors for Transient and Stable Expression of Recombinant Proteins", BioTechniques, 1993, vol. 15, No. 2, pp. 255-259.

Lang, Z., et al., "An Autonomously Replicating Eukaryotic Expression Vector with a Tetracycline-Responsive Promoter", Gene, 1996, vol. 168, pp. 169-171.

Cho, M-S., et al., "An *ori*P Expression Vector Containing the HIV-1 Tat/TAR Transactivation Axis Produces High Levels of Protein Expression in Mammalian Cells", Cytotechnology, 2001, vol. 37, pp. 23-30.

* cited by examiner

*Primary Examiner*—Maria Marvich
(74) *Attorney, Agent, or Firm*—Connolly Bove Lodge & Hutz, LLP

(57) ABSTRACT

A mammalian cell gene expression vector system comprising (a) an episomal maintenance system (b), a strong promoter/enhancer, (c) a protein transactivation system and (d) DNA coding for a heterologous protein. The episomal maintenance and protein transactivation systems can include sub-elements located on the same or different plasmids within the cell expression system.

11 Claims, 6 Drawing Sheets

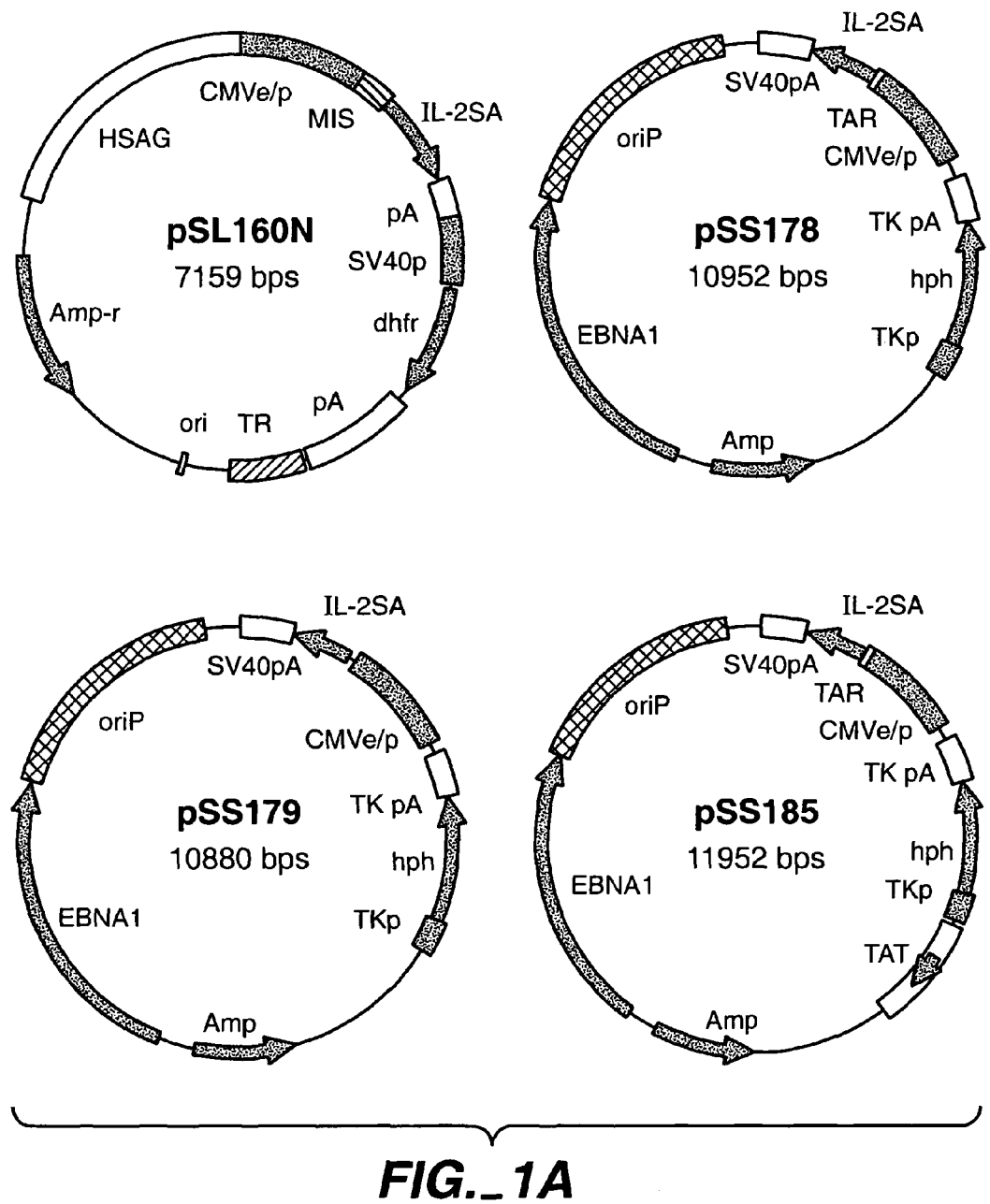
FIG._1A

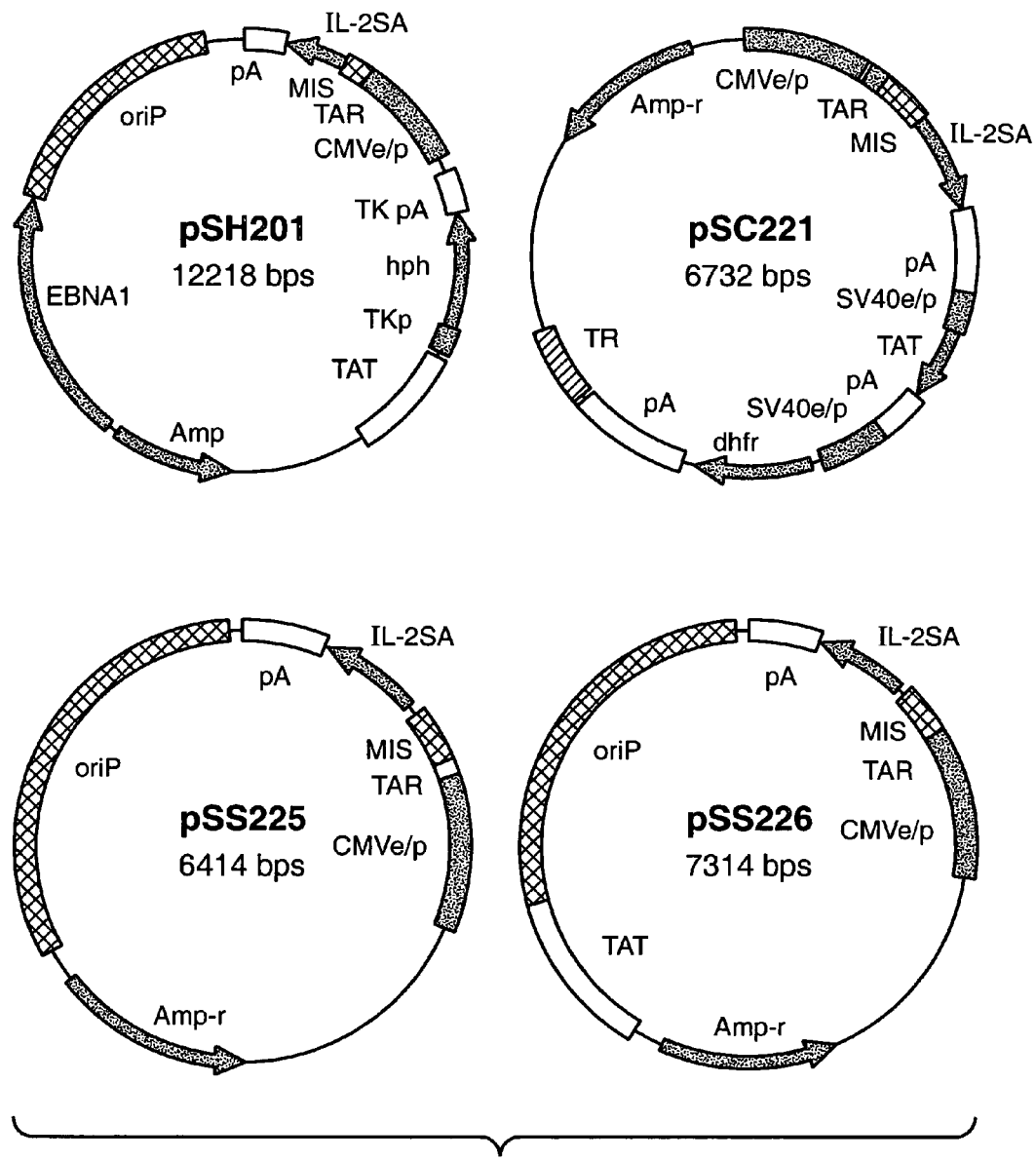
FIG._1B

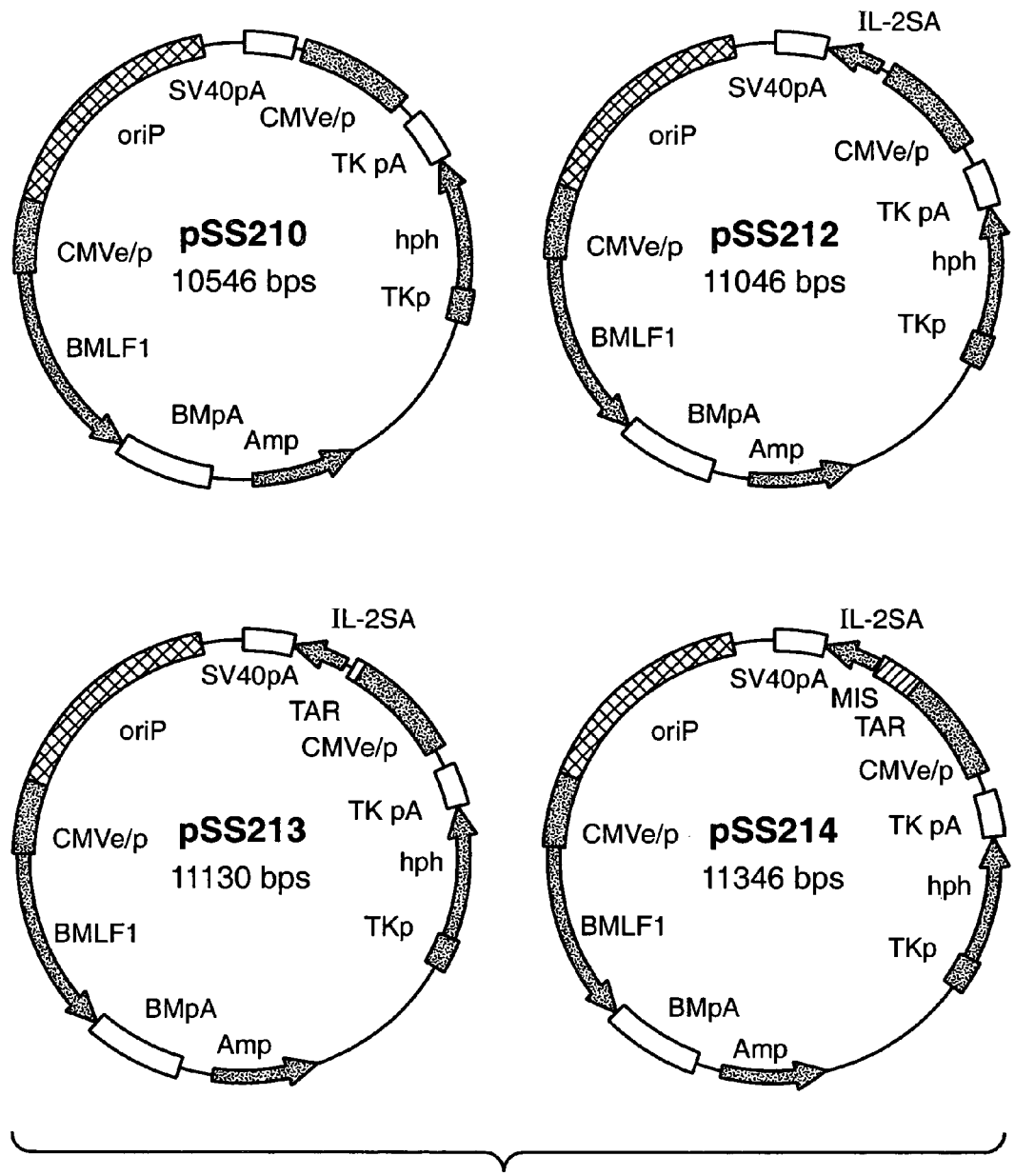
FIG._2

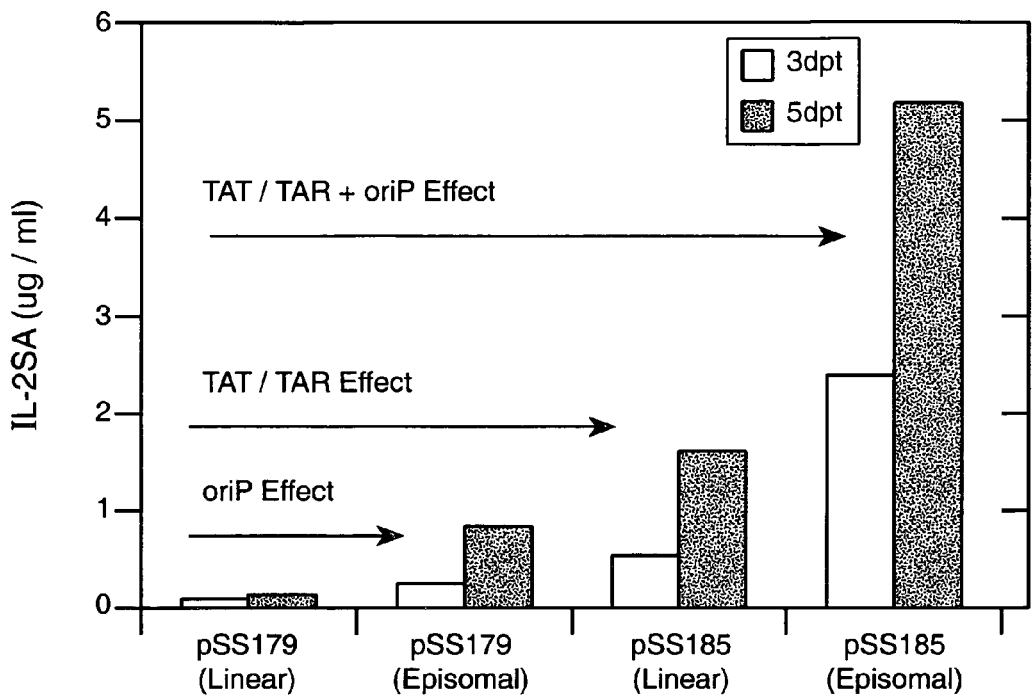
*FIG._3*
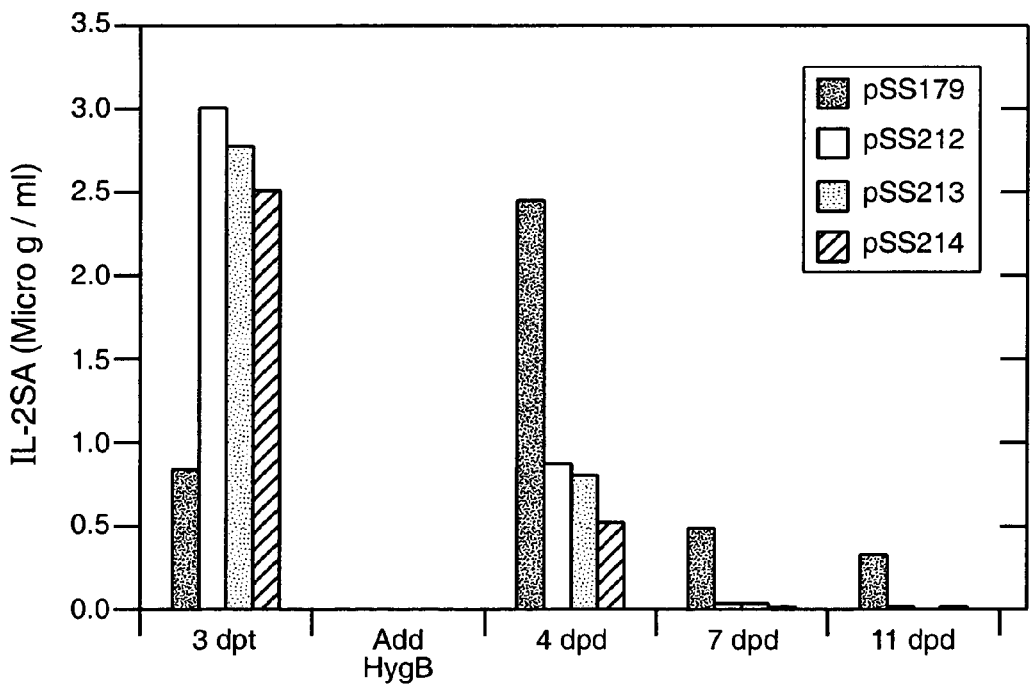
*FIG._4*

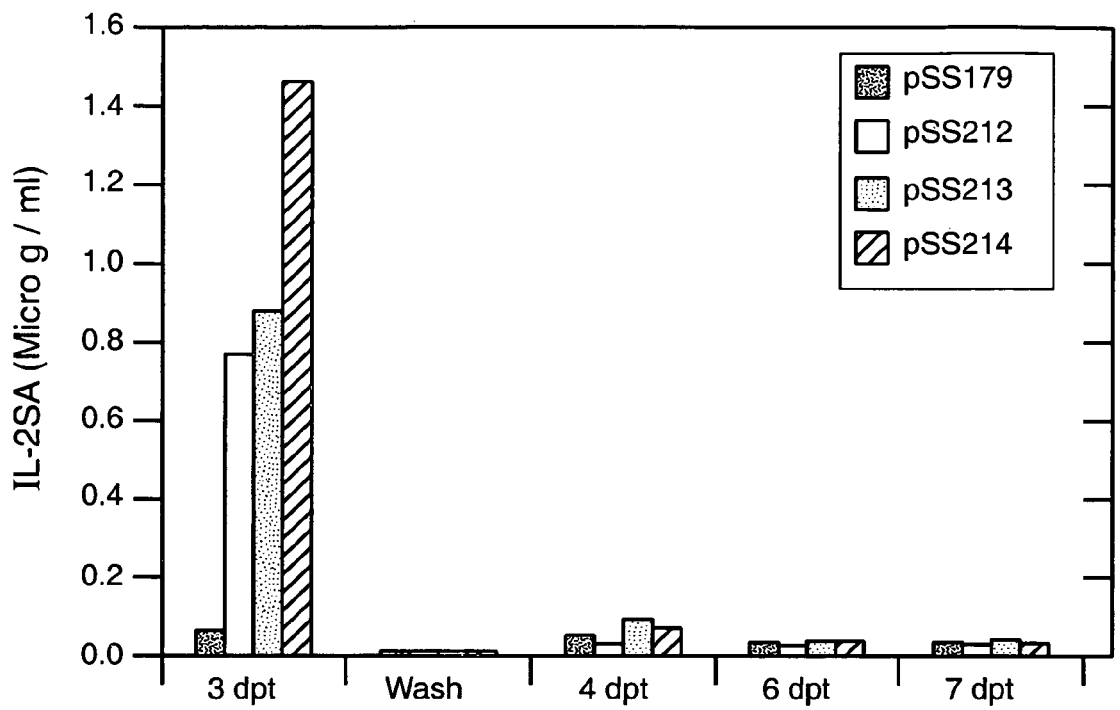
FIG._5
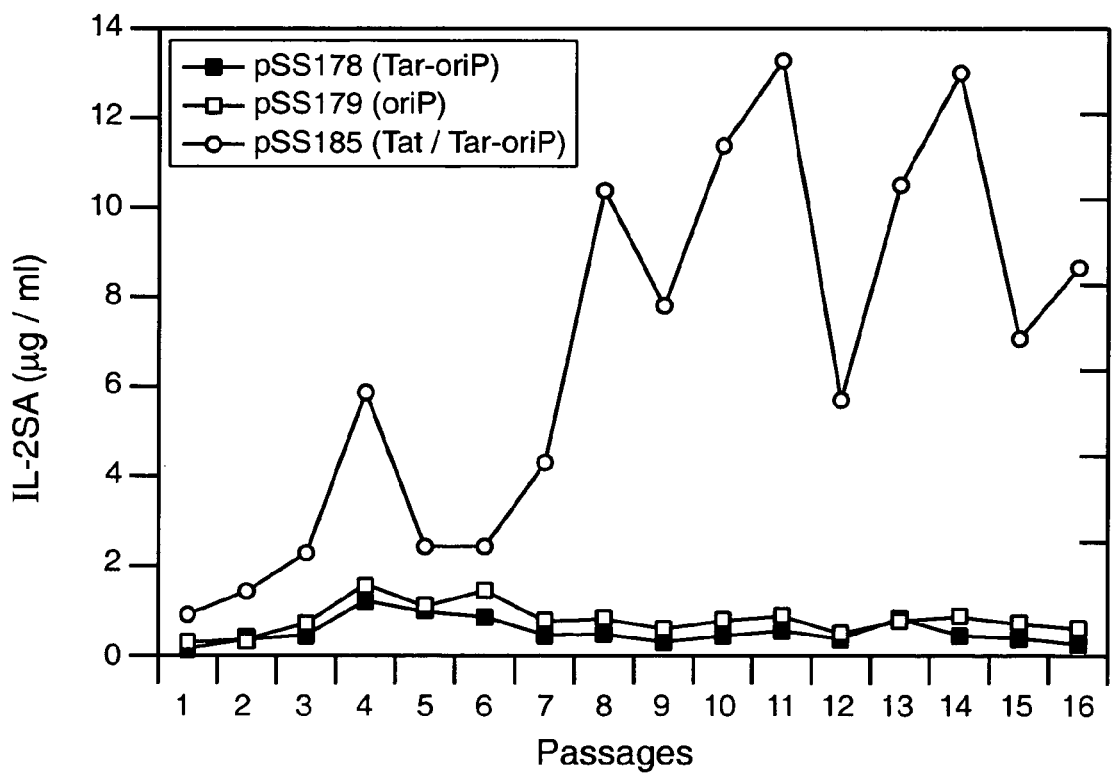
FIG._6

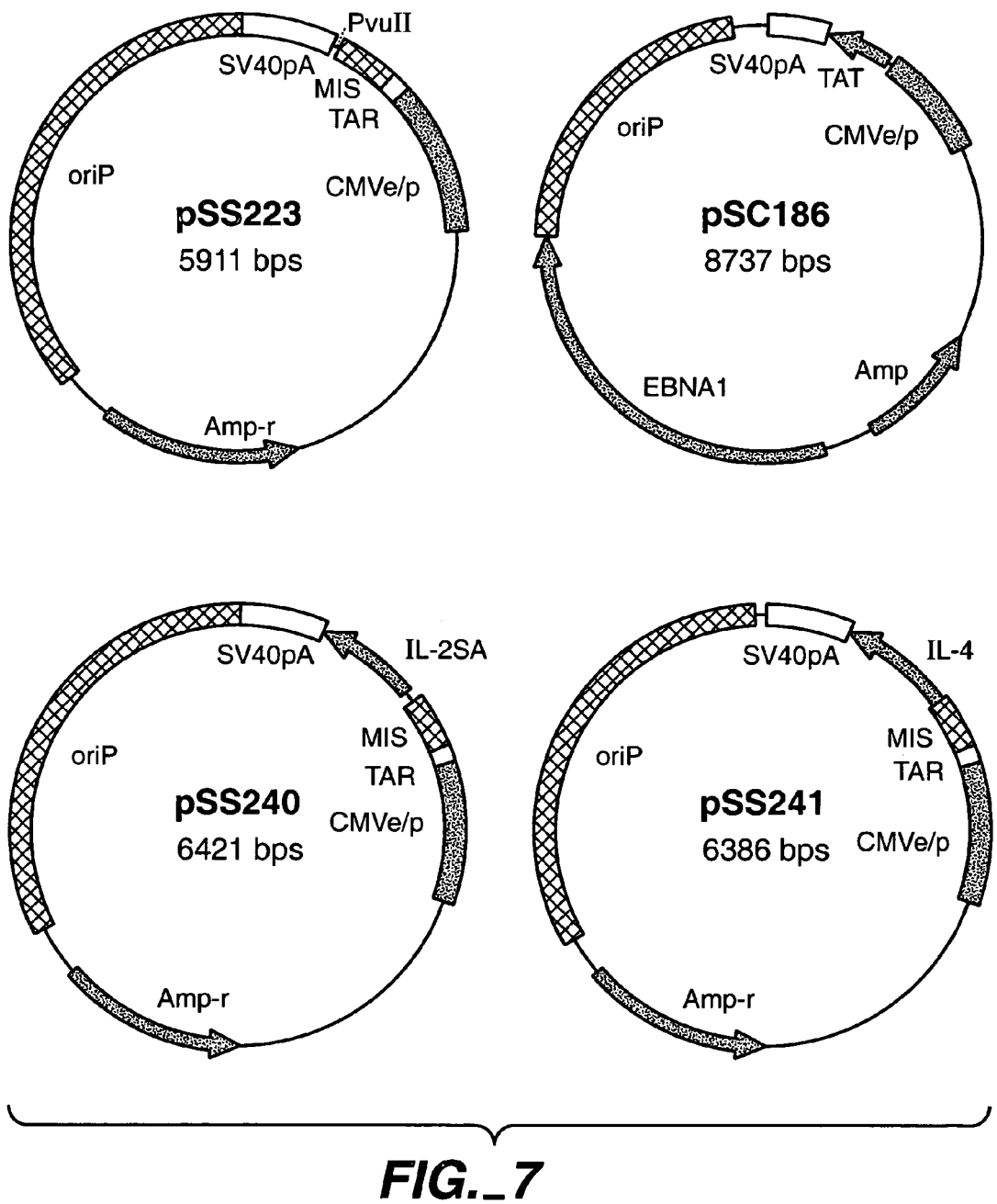
FIG._7

ENHANCED TRANSFECTION SYSTEM

CROSS REFERENCE TO RELATED APPLICATIONS

This Application claims priority to provisional application 60/386,223 filed Sep. 28, 2000.

FIELD

This invention generally relates to an improvement in mammalian cell expression systems and specifically relates to a mammalian cell gene expression vector system which includes an episomal maintenance system, a strong promoter/enhancer, a protein transactivation system and DNA coding for a heterologous protein.

BACKGROUND

It is well known that various cell hosts such as microbial cells, yeast cells, insects cells and mammalian cells are capable of producing small amounts (milligram quantities) of specific proteins in relatively short periods of time. Also, it is known that proteins from different genetically engineered host cell systems generate proteins having different glycosylation profiles, depending on the cell used. For pharmaceutical applications in some cases it is desirable to product proteins that have glycosylation profiles that are similar to those found in humans. This is usually accomplished using a mammalian cell system since such systems produce proteins with glycosylations that are compatible with clinical applications. The disadvantage of using mammalian cells is that they typically require a longer period of time to produce an equivalent quantity of protein. Thus, it would be very desirable to have a genetically engineered mammalian cell expression system (for expressing heterologous proteins) that can express larger amounts of the protein in shorter periods of time.

It is known that various episomal maintenance elements can be introduced into a vector in a gene expression system to ensure replication. It is also well known that genetically engineered systems can and in many cases should include strong promoter/enhancer systems. In addition, it is well known that genetically engineered cell lines can include protein transactivation systems to enhance protein expression from DNA coding for a heterologous protein that is also incorporated into the system. Against that background, we are unaware of any attempts or suggestions to incorporate all four of the above elements or systems into a single mammalian cell expression system so that the combined advantages of all of the elements are present in a single and functioning system that expresses heterologous proteins. To our surprise, when the above combination was made using the techniques described below we found what appears to be a synergistic effect on protein expression. Representative examples for two heterologous proteins (designated IL-2SA and IL-4SA) are described below.

SUMMARY OF THE INVENTION

Our mammalian cell gene expression vector system comprises:
(a) an episomal maintenance system,
(b) a strong promoter/enhancer,
(c) a protein transactivation system, and
(d) DNA coding for heterologous protein.

The episomal maintenance system and the protein transactivation system can include sub-elements that are located on same or different plasmids within the mammalian cell expression system. In a preferred system, the episomal maintenance system comprises of an oriP element and an EBNA1 expressing gene. A preferred strong promoter/enhancer is CMV and the preferred protein transactivation system includes both TAT and TAR elements. A preferred DNA coding sequence for the heterologous protein includes DNA that codes for substances (described in more detail below) known as IL-2SA and IL-4SA. A preferred mammalian cell line comes from a primate although other mammalian cell lines can be used. It should be noted, however, that the preferred cell lines should be non-rodent for reasons given below.

The components used to demonstrate our systems are described below.

1. A pBR322-based expression vector was supplemented with human CMV enhancer/promoter element and 5'-IS for mammalian cell expression, this plasmid is pSM97 (described in U.S. Pat. No. 5,854,021).

2. EBNA1 and oriP elements, which can support maintenance of plasmid DNA as an episomal structure (Yates et al., Proc. Natl. Acad. Sci. USA 81:3806-3810 and U.S. Pat. No 4,686,186), were added to the above expression vector.

3. TAT (transactivator gene) and TAR (trans-activating responsive sequence) elements, which can support the transactivating function of TAT protein (described in U.S. Pat. No. 5,801,056), designated them here as TAT/TAR elements, were added to the expression vector to result in an oriP expression vector combined with the TAT/TAR elements.

4. BMLF1 transactivator (Lieberman et al., J Virol 60:140-148, 1986, Kenney et al., J Virol, 63: 3870-3877, 1989, and Ruvolo et al., Proc. Natl. Acad. Sci. USA 95: 8852-8857) originated from Epstein-Barr virus was inserted into vector.

BRIEF DESCRIPTION OF THE FIGURES

FIGS. 1A and 1B show physical maps of Interleukin-2 mutein (designated IL-2SA) expression vectors used for the transfection study of the optimization of expression vectors, which included combined oriP and TAT/TAR elements.

FIG. 2. shows physical maps of expression vectors used for the transfection study of BMLF transactivation effect.

FIG. 3 is a chart which shows enhancement of IL-2SA secretion in transient transfection assays used to identify and compare oriP effect, TAT/TAR transactivation effect, and TAT/TAR transactivation plus oriP effects. Note that we assumed the linearized pSS179 as base line of IL-2SA expression level because oriP function should be abolished after linearization by using a restriction enzyme and similarly with linearized pSS185.

FIG. 4 shows BMLF1 transactivation effects on IL-2SA secretion from CHO cells in a prolonged culture time. At 3 dpt, cells were treated with trypsin and seeded with the same numbers of cells on a well with a fresh medium supplemented with 5% FBS. The secretion levels of IL-2SA from pSS179 transfected CHO cells maintained similarly throughout 4-7 dpt with that from 3 dpt. However, IL-2SA expression levels from pSS212, 213, and 214 transfected CHO cells after 4 dpt didn't show any enhanced effect of BMLF1 transfection activity that was shown at 3 dpt.

FIG. 5 shows BMLF1 transactivation effects on IL-2SA secretion from HKB11 cells in a prolonged culture time under the drug selection. BMLF1 transactivation effects seen at 3 dpt, from HKB11 cells transfected with pSS212, 213, and 214, was abolished after adding HygB, although TAT/TAR effect was maintained under the drug selection as shown in FIG. 6.

FIG. 6 shows TAT/TAR transactivation effects on IL-2SA secretion from HKB11 cells under the hygromycin B selection. The transfected cells were maintained as described in the text.

FIG. 7 shows physical maps of expression vectors used for cotransfection study for highthroughput expression.

SPECIFIC EMBODIMENTS

Materials and Methods

Cells

Human embryonic kidney cells (293) (ATCC CRL-1573) 293EBNA (EBNA1 expressing 293 cells) obtained from Invitrogen (Carlsbad, Calif.)

Dihydrofolate reductase (dhfr)-negative CHO (Chinese Hamster Ovary) cells were obtained from Genentech Inc.

HKB11 (ATCC, CRL-12568) is a human somatic hybrid cell line (U.S. patent application Ser. No. 09/209,920) derived from the cell fusion of human embryonic kidney (293S) cells and Burkitt's lymphoma origin (P3HR-1) cells.

Plasmids Construction

The IL-2 SA is an IL-2 mutein having a single amino acid substitution (N88R), as described in WO 99/60128. A brief description of the individual expression vectors of FIGS. 1-1 and 1-2 is as follows.

pSL160N: IL-2SA coding sequence was inserted into PvuII site of pSM97 and further modified by adding HSAG1 element (EcoRI and XbaI fragment; 1447 bp) described in McArthur and Stanners (J Biol Chem 266: 6000-6005, 1991) into SpeI site of pSM97 and EBV-TR (Cho et al., U.S. patent application Ser. No. 09/209,915) into NaeI site of pSM97.

pSS179: IL-2SA coding sequence was inserted into BamHI/XhoI site of pCEP4.

pSS178: TAR element (82 bp) is located upstream of IL-2SA of pSS179.

pSS185: A functional TAR element described in the plasmid construction was inserted into NruI site (upstream site of TK promoter) of pSS178.

pSH201: An intronic sequence, MIS (~270 bp) was located at the 3'-end of TAR sequence (NotI/HindIII) of pSS185.

pSC221: HSAG element of pSL160N was omitted and TAR element was located at 3'-end of CMVe/p and 5'-end of MIS.

pSS225: EBNA1 and functional TAT and hph expressing segments were excised from pSH201.

pSS226: A functional TAT expressing element was inserted at 5'-end of amp-r gene of pSS225.

A description of individual expression vector of FIG. 2 is as follows.

pSS210: BMLF1 and hph expressing oriP plasmid was described in a section of plasmid contruction.

pSS212: IL-2SA coding sequence was located 3'-end of CMVe/p of pSS210.

pSS213: A TAR element is located at the 5'-end of IL-2SA of pSS212.

pSS214: An intronic sequence, MIS, is further added at the 5'end of IL-2SA of pSS213.

A brief description of individual plasmid structure of FIG. 7 is as follows.

pSS223: This plasmid is basically same as pSS225 but missing IL-2SA coding sequence.

pSC186: A TAT coding sequence was located at the 3'-end of CMVe/p of pCEP4 and the functional hph expressing segment was deleted.

pSS240: IL-2SA coding sequence was inserted into PvuII site of pSS223.

pSS241: IL-4 coding sequence was inserted into PvuII site of pSS223.

The pBR322-based mammalian cell expression vector with a functional dhfr gene expression (pSM97; Cho et al., U.S. Pat. No. 5,854,021). pCEP4 vector consisting of oriP, EBNA1, and functional hph gene expression based on pBR322 was obtained from Invitrogen (Carlsbad, Calif.).

Eighty-two base pairs of TAR element was prepared by PCR using pBennCAT (Gendelman H. E. et al., Proc. Natl. Acad. Sci. USA 83:9759-9763, 1986) as a template. Two primers were made by adding KpnI site at 5'-end of TAR and HindIII site at 3' end of TAR. The resulting PCR product was digested with HindIII and KpnI and inserted into pCEP4 after digesting pCEP4 with KpnI and HindIII. The functional TAT gene expressing segment was prepared from pSVTAT (Peterlin B. M. et al., Proc. Natl. Acad. Sci. USA 83: 9734-9738, 1986) by digesting it with BamHI (modified with Klenow fragment) and HpaI.

This fragment was inserted to $pSV_2neo$ after digesting with PvuII and HpaI. This functional TAT expressing segment can be easily excised by digesting with PvuII and BamHI to insert into any other expression vectors as shown in FIG. 1 (pSS185 and pSC221). BMLF1 coding sequence and polyA signal area was prepared from B95-8 EBV encompassing DNA sequence from 84301 (NheI) to 82180 (HindIII) of B95/8 EBV sequence data (P. J. Farrell, "Epstein-Barr Virus Genome" in Advanced Viral Oncology; edited by G. Klein; Ravens Press, Ltd.: New York 1989, pp 103-132) and inserted to PvuII site of pCEP4, a vector with CMVe/p. This BMLF1 expression is now under the control of CMVe/p.

The functional BMLF1 expression segment was removed by digestion with SpeI and NheI from this vector and a new expression vector was constructed. This resulting plasmid pSS210 found in FIG. 2. The Interleukin-2 mutein (N88R) known as IL-2SA (Patent application file No. WO9960128, IL-2 Selective Agonists and Antagonists) was used as a reporter gene.

Transfection

Stationary transfections were performed using the cells growing in anchorage dependent mode. Logarithmically growing HKB11 cells ($1.5 \times 10^6$ cells) in 4 ml of fresh medium with either 5% FBS or without serum were seeded in one well of a 6-well format tissue culture dish (Corning Inc., Corning, N.Y.) and allowed to attach on the bottom of the plate for two or more hours in a humidified CO2 incubator at 37° C. A cocktail (1 ml) consisting of 5 μg of DNA and 20 μl of DMRIE-C reagent (Life Technologies, Rockville, Md.) was prepared according to the manufacturer's protocol and added to the well and mixed gently. Plates were incubated in the CO2 incubator.

Shaking transfections were performed using cells adapted to serum-free suspension conditions. Logarithmically growing HKB11 cells ($5 \times 10^6$ cells) in 4 ml of fresh medium were mixed with one ml of the DNA/DMRIE-C complex as in the above stationary transfection. This 5 ml of transfected cells in a 6-well format was incubated on a shaker (90-100 rpm) in a humidified $CO_2$-incubater. Transfected cells were sub-cultured at 3 and 7 days post transfection (dpt) by splitting either 1:4 or 1:5. The total culture volume was increased from the initial transfection volume to 20 fold at 10 dpt. Tissue culture supernatant was analyzed by an ELISA to determine secretion levels of proteins.

ELISA

For detection of IL-2SA, Dynatech Immulo-2 round bottom plates were coated with 1 µg/ml purified anti-human IL-2 (PharMingen, San Diego, Calif.) from rat using 0.1 M NaHCO$_2$ (pH 8.2) buffer, incubated at 37° C. for 3 hours in a humidified chamber, washed with PBS/0.05% Tween 20 (Sigma P-1379, St Louis, Mo.) and blocked with PBS/1% BSA for one hour at room temperature. Culture supernatants containing IL-2SA and a standard of purified IL-2SA (as a standard curve) were serially diluted with PBS/1% BSA (50 µl/well) and incubated at room temperature for two hours. Captured IL-2SA was detected using biotinylated mouse anti-human IL-2 (62.5 ng/ml; PharMingen, San Diego, Calif.) followed by incubation with HRP-streptavidin (125 ng/ml; Zymed Laboratories Inc. #43-4323, South San Francisco, Calif.). Between all incubations (a one hour incubation each at room temperature), plates were washed with PBS/Tween 20. Plates were developed using substrate solution tetramethylbenzidine (TMB; Kirkegaard & Perry Laboratories, Inc. Product# 50-65-00 and 50-76-01, Gaithersburg, Md.) and the reaction was stopped with 1 N HCl. The optical density (OD) was measured at 450 nm/570 nm using Molecular Device's Vmax kinetic microplate reader (S/N 04514, Sunnyvale, Calif.) and the Softmax program provided by Molecular Devices. The IL-2SA concentration in the tissue culture supernatant was determined by comparing to the OD of a standard curve of purified IL-2SA.

To measure human interleukin-4 (IL-4) secretion, assay was similar except mouse anti human IL-4 antibody (PharMingen, Cat. #18651D, San Diego, Calif.) was used to coat the plate, and biotinylated anti rat IL-4 antibody (PharMingen, Cat. #18502D, San Diego, Calif.) was used as a detection antibody. Purified IL-4 molecule was used as a standard.

EXAMPLE 1

Protein Expression in Transient Transfection Assays Using TAT/TAR-oriP Expression Vectors Mammalian cell expression vectors equipped with CMVe/p in pBR322 plasmid showed relatively high level expression and secretion of between 1-20 µg/ml of heterologous protein. However, some proteins had been very difficult to express, e.g. IL-2SA. Therefore, we constructed various expression vectors equipped with different enhancing elements, mainly transactivating proteins and the oriP element to maintain the transferred plasmid as an episome. Either element alone showed a small level of increases (3-5 fold) in transient transfection assays. We constructed two expression vectors, one with IL-2SA in pCEP4 vector (pSS179) and other with the addition of TAT/TAR transactivating elements to the pSS179 (pSS185). Both IL-2SA expressing plasmid DNAs (pSS179 and pSS185) were digested with restriction enzymes and the same amount of DNAs (5 µg each) of both and uncut plasmids were transfected. A small amount of both restriction enzyme digested DNAs was used to confirm the amount of precipitated DNA to assure that same amounts and quality (to see 100% conversion to linear form) were used in each transfection. Transfections were performed using stationary transfection method with medium supplemented with 5% FBS. Expression levels of each plasmid were analyzed the under assumption that the linear form of plasmid abolishes oriP function, because linear DNA can not be replicated at this condition. Although oriP and TAT/TAR have an enhancing effect, when evaluated individually under the regulation of a CMV promoter, the increase is considerably low (3-5 fold) in transient transfection assays.

As shown in FIG. 3, the effects of oriP element (uncut pSS179) and TAT/TAR transactivation (cut pSS185) on IL-2SA secretion were 2.7 and 6 fold, respectively, higher than that from linear form of pSS179 at 3 dpt. The fold increases at 5 dpt was 5.6 and 10, respectively. However, the uncut pSS185 (intact TAT/TAR transactivation and oriP function) showed unexpectedly higher levels (26 fold at 3 dpt and 34 fold at 5 dpt) of IL-2SA secretion than that from cut pSS179.

We tested also other vector constructions consisting of same functional element. IL-2SA expressing vectors pSC221 (TAT/TAR-dhfr), pSH201(TAT/TAR-oriP with EBNA1), and pSS226(TAT/TAR-oriP w/o EBNA1) were used to transfect HKB11 and 293EBNA cells to compare two host cells and to compare episomal vectors of TAT/TAR and TAT/TAR-oriP. See FIG. 1 for the physical maps of the expression vectors. As shown in Table 1, the TAT/TAR-oriP effect (pSH201) over TAT/TAR (pSC221) was ~9-fold higher in HKB11 cells and ~4-fold higher in 293EBNA cells at 3 dpt. This effects was similar as that (4.4-fold) we observed using episomal and linear pSS185 (FIG. 3). 293EBNA cells showed slightly lower secretion levels of IL-2SA than HKB11 cells, however, it was clear that TAT/TAR-oriP vector can be used in other than HKB11 cells, here 293EBNA cells, for maximal protein production. We observed that TAT/TAR-oriP vector equipped with EBNA1 gene was slightly better than withoutEBNA1 gene. It seems that HKB11 and 293EBNA cells may not have enough EBNA1 protein to maintain episomal vector.

We also tested other vector constructions consisting of the same functional element. IL-2SA expressing vectors pSC221 (TAT/TAR-dhfr), pSH201(TAT/TAR-oriP with EBNA1), and pSS226(TAT/TAR-oriP w/o EBNA1) were used to transfect HKB11 and 293EBNA cells to compare two host cells and to compare episomal vectors of TAT/TAR and TAT/TAR-oriP. See FIG. 1 for the physical maps of the expression vectors. As shown in Table 1, the TAT/TAR-oriP effect (pSH201) over TAT/TAR (pSC221) was ~9-fold higher in HKB11 cells and ~4-fold higher in 293EBNA cells. This effects were similar (~5-fold) to what we observed using episomal and linear pSS185 (FIG. 2). 293EBNA cells showed slightly lower secretion levels of IL-23SA than HKB11 cells, however, it was clear that TAT/TAR-oriP synergistic effect was also observed in 293EBNA cells aside from HKB11 cells, for maximal protein production. We observed that TAT/TAR-oriP vector equipped with EBNA1 gene was slightly better than without EBNA1 gene. It seems that HKB11 and 293EBNA cells may not have enough EBNA1 protein to maintain episomal vector.

TABLE 1

Comparison of HKB11 and 293EBNA cells transfected with TAT/TAR and TAT/TAR-oriP vectors for IL-2SA secretion in serum-free medium at 3 dpt.

| Expression | HKB11 | | 283EBNA | |
|---|---|---|---|---|
| vector | Titer (µg/ml) | Fold increase | Titer (µg/ml) | Fold increase |
| pSC221 | 0.5 | 1 | 0.62 | 1 |
| pSH201 | 4.45 | 8.9 | 2.55 | 4.11 |
| pSS226 | 2.98 | 5.9 | 2.27 | 3.6 |

Note:

TABLE 1-continued

Comparison of HKB11 and 293EBNA cells transfected
with TAT/TAR and TAT/TAR-oriP vectors for IL-2SA
secretion in serum-free medium at 3 dpt.

| Expression | HKB11 | | 283EBNA | |
|---|---|---|---|---|
| vector | Titer (μg/ml) | Fold increase | Titer (μg/ml) | Fold increase |

Fold increase of IL-SA by TAT/TAR and TAT/TAR-oriP was calculated from by assuming IL-2SA production from pSC221 as 1

EXAMPLE 2

Protein Expression in Transient Transfection Assays Using BMLF1-oriP Expression Vectors BMLF1 was originally known as a promiscuous transactivator (Lieberman et al., J Virol 60:140-148, 1986). Since then, this protein has been found to be post-transcriptional transactivator (Kenney et al., J. Virol, 63:3870-3877, 1989), and most recently described as a transactivator for intronless gene expression and as an inhibitor for intron linked gene expression (Ruvolo et al., Proc. Natl. Acad. Sci. USA 95: 8852-8857). We tested the BMLF1 protein for transactivating function of mammalian gene expression (IL-2SA). The IL-2SA coding sequence without 5'-IS inserted in downstream of CMVe/p of pSS210 is pSS212. IL-2SA expressing coding sequence was modified by adding TAR sequence at the 5'end of IL-2SA (pSS213) and further modified by adding an intronic sequence (MIS) at 5-end of IL-2SA of pSS213, resulting in vector pSS214. See FIG. 2 for physical maps of individual expression vector. Stationary transient transfection assays indicated that BMLF1 protein enhanced IL-2SA expression regardless of intron by 3-4 fold in HKB11 (Table 2) and by 10-20 fold in CHO cells (Table 3) using serum-containing medium.

TABLE 2

Comparison of IL-2SA production (3 dpt) from HKB11
cells transfected with various IL-2SA
expressing vectors in serum-containing medium.

| Expression | IL-2SA titers (μg/ml) | | | Fold Increase |
|---|---|---|---|---|
| Vectors | Exp. I | Exp. II | Exp. III | (Average) |
| pSS179 | 0.84 | 1.24 | 0.27 | 1 |
| pSS212 | 3 | 4.4 | 1.23 | 4 |
| pSS213 | 2.76 | 4.16 | 0.81 | 3.2 |
| pSS214 | 2.48 | 3.1 | 1.1 | 3.2 |

Note:
Fold increase of IL-2SA production by BMLF1 was calculated from the average of three experiments by assuming IL-2SA production from pSS179 as 1.
As described in FIG. 3, pSS212, pSS213, and pSS214 have IL-25A expressing segments equipped at 5' end of the molecule with intron-less, intron-less with TAR, and TAR-MIS, respectively.

TABLE 3

Comparison of IL-2SA production (3 dpt) from CHO
cells transfected with various IL-2SA expressing
vectors in serum-containing medium.

| Expression | IL-2SA titers (μg/ml) | | | Fold increase |
|---|---|---|---|---|
| Vectors | Exp. I | Exp. II | Exp. III | (average) |
| pSS179 | 0.062 | 0.058 | 0.042 | 1 |
| pSS212 | 0.275 | 0.77 | 0.7 | 11.2 |
| pSS213 | 0.23 | 0.88 | 1.33 | 16.6 |
| pSS214 | 0.225 | 1.46 | 1.52 | 21.5 |

Note:
Fold increase and expression vectors are described in Table 2.

EXAMPLE 3

Protein Production in Prolonged Transient Transfection Assays

To make larger amount of proteins, we tested these transactivating proteins in oriP plasmid in prolonged culture time post transfection up to 10 days. In this experiment, we used a basic expression vector of IL-2SA (pSL160N), an IL-2SA expression vector supplemented with TAT/TAR transactivating elements (pSC221), an IL-2SA expression vector with oriP element alone (pSS225), and IL-2SA expression element with both TAT/TAR transactivating elements and oriP element (pSS185). See FIG. 1 for the physical maps of the plasmid structure. HKB11 cells adapted to serum-free suspension condition were transfected under shaking transfection method as described earlier. The transfected cells were sub-cultured using serum-free medium by splitting 4-5 fold twice at 3 dpt and 7 dpt through 10 days period post transfection. The total transfected culture volume was increased by 20-25 fold.

We observed that the oriP effect and TAT/TAR transactivation effects (Table 4) were slightly different than the data shown in FIG. 3, which might be explained by the different plasmid states of linear form of oriP-plasmid DNA (e.g. linearized pSS179 and pSS185) and plasmid structure without oriP element (e.g. pSL160N and pSS221). For example, a baseline expression vector of linear pSS179 was assumed to show the same result with pSL160N and linear pSS185 was assumed to be the same as pSC221 because of interrupted oriP function by linearizing the plasmid structure. However, the combined effect of TAT/TAR and oriP function was similar. During this prolonged culture time, as shown in Table 4, the increase seen in protein expression (IL-2SA titers) was maintained without drastically decreased expression-levels. The total yield of IL-2SA production from pSS185 (IL-2SA expressing vector with TAT/TAR and oriP elements) in the prolonged transient transfection time (10 days) showed extremely high yield of the protein (460.8 μg) from 5 μg of transfected DNA with $5 \times 10^6$ starting cell number, while the non-optimized expression vector (pSL160N) in 3 day-culture using the same amounts of DNA and cells can harvest only 28.8 μg of the protein at 10 dpt and 1.4 μg of protein at 3 dpt using a standard expression vector.

This system was shown to be easily scaled up for the use of efficient production of proteins, e.g. when $50 \times 10^6$ HKB11 cells (50 ml culture) were transfected with 50 μg of pSS185, we could obtain approximately 5 mg of protein at 10 days post transfection with a final culture volume of one liter. In our experience, we found that this effect is proportional and that production of protein from 500 μg of DNA using shake flask was approximately 100 fold more than what was found in a standard transfection using 5 μg DNA in 6-well format. This result of lager scale transfection indicates that we can save in the cost of DNA preparation and transfection reagents using this prolonged scale up transfection system when compared to standard transfection system which use 20-25 fold more initial materials (DNA, transfection reagent, and cells).

As shown in FIGS. 4 and 5, BMLF1 transactivator could not be utilized in a prolonged transfection system, because the titers of IL-2SA and cell number decreased drastically after 3 dpt and. The BMLF1 protein might be toxic, ultimately, to the BMLF1 expressing cells in the prolonged transient transfection mode.

TABLE 4

Comparison of IL-2SA production in a prolonged and scaled-up transient transfection system using various expression vectors under serum-free condition.

| Expression vectors | Titer (μg/ml) | | | Total yields (μg) | | |
|---|---|---|---|---|---|---|
| | 3 dpt | 7 dpt | 10 dpt | 3 dpt | 7 dpt | 10 dpt |
| pSL160N | 0.28 | 0.36 | 0.36 | 1.4 | 7.2 | 28.8 |
| pSS221 | 0.64 | 0.68 | 0.74 | 3.2 | 13.6 | 58.2 |
| pSS225 | 1.22 | 1.42 | 1.31 | 6.1 | 28.4 | 104.8 |
| pSS185 | 5.08 | 7.29 | 5.76 | 25 | 145.8 | 460.8 |

Note:
Total yields indicate a multiplication of IL-2SA titers (μg/ml) by volume (ml).
pSL160N: IL-2SA coding sequence in a dhfr vector
pSS221: IL-2SA coding sequence in a TAT/TAR vector
pSS225: IL-2SA coding sequence in an oriP vector
pSS185: IL-2SA coding sequence in a TAT/TAR-oriP vector.
Cells were split 1:4 at 3 dpt and 1:5 at 7 dpt.

EXAMPLE 4

Protein Expression under the Drug Selection

IL-2SA expression from oriP vectors, pSS178 and pSS179 (see FIG. 1 for physical maps of the plasmids), were tested and compared to IL-2SA expression from a TAT/TAR-oriP vector, pSS185, under the drug selection to obtain drug resistant cells for larger scale protein production for even longer periods of time. HKB11 cells growing in a shake flask under serum-free condition were transfected with the three expression vectors using 6-well format. Three days post transfection, transfected cells were inoculated into a shake flask, $2 \times 10^6$ cells in 20 ml of serum (5%) containing medium supplemented with 100 μg/ml of hygromycin B (HygB). Cells were sub-cultured twice per week using this same selection media. Cells were centrifuged and resuspended in the same volume of fresh medium in the first three passages. After this initial selection phase, cell culture were sub-cultured by maintaining cell density of $5 \times 10^5$ cells/ml. Titers of IL-2SA production from each passage were measured by an ELISA. Four weeks post production the IL-2SA productivity from pSS185 was maintained at higher titer than those from pSS178 and pSS179 by over 10 fold (FIG. 6). These results indicate that TAT/TAR transactivating elements with oriP elements together (pSS185) under drug selection system show much higher productivity when compared to IL-2SA productivity from oriP vectors, pSS178 and pSS179.

EXAMPLE 5

TAT/TAR-oriP System for Highthroughput Transfection

Although the TAT/TAR-oriP expression vector showed unexpectedly high expression of protein, the size of the vector is too large to use in high throughput cloning. Therefore, we separated the expression vector into two functional groups. The main cloning vector (5.9 kb) consists of CMVe/p, TAR, MIS, cloning site (PvuII) and polyA signal in an oriP vector, pSS223. The TAT expressing oriP vector (8.7 kb) pSC186 plasmid was co-transfected plasmid. In transient transfection assays for high throughput screening, we can transfect 5 μg of pSS223 with the gene of interest and 1 μg of TAT expressing oriP plasmid pSS186. As shown in FIG. 7, we inserted the IL-2SA and IL-4 coding sequences into PvuII cloning site of pSS223. The resulting plasmids are pSS240 and pSS241, respectively. HKB11 cells were co-transfected with 5 μg of pSS240 or pSS241 and 1 μg of pSC186 in a shaking transfection mode under serum-free condition. We observed a similar result of 3-5 fold increase in cotransfection assays (Table 5) as in TAT/TAR-oriP vector (pSS185) over oriP vector (pSS225) (Table 4). This result indicates that the cotransfection method of the two functionally separated plasmids is equivalent to the transfection of the single expression vector consisting of both TAT/TAR and oriP elements.

TABLE 5

Comparison of protein production (μg/ml) from TAR-oriP vector to those from the cotransfection with TAT-oriP vector

| | Single transfection | Cotransfection with pSC186 | Fold increase |
|---|---|---|---|
| IL-2SA (3 dpt) | 4.28 | 14.2 | 3.3 |
| IL-2SA (6 dpt) | 3.07 | 15.9 | 5.1 |
| IL-4 (3 dpt) | 13.4 | 41.6 | 3.1 |
| IL-4 (6 dpt) | 11.6 | 37.2 | 3.2 |

Note:
Fold increase was calculated from the cotransfection values over the values of single transfection.

DISCUSSION

Heterologous proteins expressed by mammalian cells usually have a better or more desirable qualities for characterizing the proteins than proteins expressed from non-mammalian cells and, thus, mammalian cells are preferred. However, the quantity of the protein made by mammalian cell is usually smaller than other systems. To compensate the above problems, we optimized a transient transfection system to produce "fast track" protein production. Our results are based on many factors as follows:

1. Optimized HKB11 cell host that was adapted to a serum-free suspension condition.
2. Shaking transfection methods using serum-free medium. In this method, we could use a larger initial cell density under optimal growth conditions, which can subsequently produce more protein. In stationary transfections, more than $1.5 \times 10^6$ cells per well could not be used for transfection, because of the non-optimal growth condition of cells growing as a monolayer. Using monolayer cells (e.g. CHO cells) for transfection, shaking conditions of transfected culture provided more protein secretion (2-3 fold) over non-shaking conditions, for reasons not entirely clear.
3. Optimized expression vectors using the oriP element, which can maintain transferred plasmid as episomes, and transactivation elements, which can enhance protein expression, simultaneously.
4. The most critical part and unexpected result of this improved transfection system were the combination of oriP element and TAT/TAR transactivation elements for protein expression and such combination in a single vector or transfection system has not been suggested in the prior art.

The experiment using CHO cells was not pursued intensively after obtaining the ineffective data in TAT/TAR-oriP transactivation system and based on the following published information. An oriP plasmid is not replicating efficiently (Yates et al., Nature 313:812-815, 1985 and Mizuguchi et al., FEBS lett 472:173-178, 2000) in rodent cells and CHO cell lacks cellular factors for TAT/TAR transactivation system (Alonso et al., J Virol 66:4617-4621, 1992 and Wimmer et al., Virology 255:182-189, 1999).

Given the above disclosure, it is though variations will now occur to those skilled in the art. Accordingly, it is intended that the above examples should be construed as illustrative and that the scope of the inventions disclosed herein should be limited only by the following claims.

The invention claimed is:

1. A composition comprising a plasmid, the plasmid comprising:
   a. an oriP element;
   b. a first nucleic acid sequence encoding EBNA 1 operably linked to a promoter;
   c. a second nucleic acid sequence encoding TAT operably linked to a promoter;
   d. a TAR element; and
   e. a third nucleic acid sequence encoding a heterologous protein operably linked to a first CMV promoter/enhancer.

2. The composition of claim 1, further comprising a nucleic acid sequence encoding BMLF1 operably linked to a second CMV promoter/enhancer.

3. The composition of claim 1, wherein the heterologous protein is selected from the group consisting of IL-4 and IL-2SA.

4. A method for producing a heterologous protein from a mammalian host cell, comprising the steps of:
   (a) transforming the mammalian host cell with the composition of claim 1;
   (b) expanding the host cell of step (a) in culture; and
   (c) isolating the heterologous protein from the culture of step (b).

5. A composition comprising a first plasmid and a second plasmid, wherein the first plasmid comprises an oriP element, a first nucleic acid sequence encoding EBNA1 operably linked to a promoter, and a second nucleic acid sequence encoding TAT operably linked to a promoter, and the second plasmid comprises an oriP element, a TAR element, and a nucleic acid sequence encoding a heterologous protein operably linked to a CMV promoter/enhancer.

6. The composition of claim 5 wherein the first plasmid further comprises a nucleic acid sequence encoding BMLF1 operably linked to a promoter.

7. The composition of claim 5 wherein the heterologous protein is selected from the group consisting of IL-4 and IL-2SA.

8. A method for producing a heterologous protein from a mammalian host cell, comprising the steps of:
   (a) transforming the mammalian host cell with the composition of claim 5;
   (b) expanding the host cell of step (a) in culture; and
   (c) isolating the heterologous protein from the culture of step (b).

9. A mammalian cell line transformed with a composition comprising a plasmid, the plasmid comprising:
   a. an oriP element;
   b. a first nucleic acid sequence encoding EBNA 1 operably linked to a promoter;
   c. a second nucleic acid sequence encoding TAT operably linked to a promoter;
   d. a TAR element; and
   e. a third nucleic acid sequence encoding a heterologous protein operably linked to a first CMV promoter/enhancer.

10. A mammalian cell line transformed with a composition, the composition comprising a first plasmid and a second plasmid, wherein the first plasmid comprises an oriP element, a first nucleic acid sequence encoding EBNA1 operably linked to a promoter, and a second nucleic acid sequence encoding TAT operably linked to a promoter, and the second plasmid comprises an oriP element, a TAR element, and a nucleic acid sequence encoding a heterologous protein operably linked to a CMV promoter/enhancer.

11. A mammalian cell line transformed with at least one plasmid, wherein the cell line expresses EBNA1 prior to transformation, the plasmid comprising:
   a. an oriP element;
   b. a first nucleic acid sequence encoding TAT operably linked to a promoter;
   c. a TAR element; and
   d. a second nucleic acid sequence encoding a heterologous protein operably linked to a CMV promoter/enhancer.

* * * * *